(12) United States Patent  (10) Patent No.: US 8,180,653 B2
Banfield et al.  (45) Date of Patent: May 15, 2012

(54) PHARMACY NETWORK COMPUTER SYSTEM AND PRINTER

(75) Inventors: Simon Banfield, Tierra Verde, FL (US);
Baxter Byerly, Brooksville, FL (US);
Daniel Schutte, Clearwater, FL (US)

(73) Assignee: Catalina Marketing Corporation, St. Petersburg, FL (US)

( * ) Notice: Subject to any disclaimer, the term of this patent is extended or adjusted under 35 U.S.C. 154(b) by 1699 days.

(21) Appl. No.: 11/366,397

(22) Filed: Mar. 3, 2006

(65) Prior Publication Data

US 2007/0164096 A1  Jul. 19, 2007

Related U.S. Application Data

(60) Provisional application No. 60/759,552, filed on Jan. 18, 2006.

(51) Int. Cl.
*G06F 19/00* (2011.01)
(52) U.S. Cl. .......................................................... 705/3
(58) Field of Classification Search .................. 705/2, 3, 705/4, 14, 21; 358/1.12, 1.15, 1.18
See application file for complete search history.

(56) References Cited

U.S. PATENT DOCUMENTS

| | | | |
|---|---|---|---|
| 4,980,725 A | 12/1990 | Sumida | |
| 5,456,539 A | 10/1995 | Wright et al. | |
| 5,570,451 A | 10/1996 | Sakaizawa et al. | |
| 5,666,215 A | 9/1997 | Fredlund et al. | |
| 5,688,154 A | 11/1997 | Goda et al. | |
| 5,737,729 A | 4/1998 | Denman | |
| 5,857,175 A | 1/1999 | Day et al. | |
| 5,917,513 A | 6/1999 | Miyauchi et al. | |
| 6,067,524 A * | 5/2000 | Byerly et al. | 705/3 |
| 6,076,068 A | 6/2000 | De Lapa et al. | |
| 6,151,038 A | 11/2000 | Suzuki | |
| 6,208,973 B1 * | 3/2001 | Boyer et al. | 705/2 |
| 6,231,249 B1 | 5/2001 | Harris | |
| 6,240,394 B1 * | 5/2001 | Uecker et al. | 705/3 |
| 6,351,735 B1 | 2/2002 | Deaton et al. | |
| 6,767,073 B2 | 7/2004 | Tschida | |
| 2001/0021331 A1 | 9/2001 | Brewington et al. | |
| 2002/0002495 A1 * | 1/2002 | Ullman | 705/21 |

(Continued)

FOREIGN PATENT DOCUMENTS

WO   WO 98/21713   5/1998

OTHER PUBLICATIONS

U.S. FDA CDER "The CDER Handbook" Mar. 16, 1998.* U.S. FDA CDER "2005 Report to the Nation" Aug. 18, 2006.*
"NCPDP SCRIPT Standard Presentation", Mar. 30, 2004.*
Nov. 9, 2007, PCT International Search Report PCT/US07/63051.
Nov. 9, 2007, PCT Written Opinion PCT/US07/63051.
Dec. 26, 2007, PCT International Search Report PCT/US06/26313.
Dec. 26, 2007, PCT Written Opinion PCT/US06/26313.

(Continued)

*Primary Examiner* — Gerald J. O'Connor
*Assistant Examiner* — John Pauls
(74) *Attorney, Agent, or Firm* — Pillsbury Winthrop Shaw Pittman LLP

(57) ABSTRACT

The invention provides a network computer system and novel pharmacy printers and their methods of use wherein the local CS includes a pharmacy printer for printing pharmacy orders including prescriptions, and the pharmacy printer includes a pharmacy printer database storing drug information and association of a drug identifier with information about a corresponding drug, and additional information, and obtains and uses instructions for printing the additional information in association with printing of a prescription label from characters contained in a prescription label print file for the prescription label.

31 Claims, 10 Drawing Sheets

U.S. PATENT DOCUMENTS

| | | | |
|---|---|---|---|
| 2002/0129002 | A1 | 9/2002 | Alberts et al. |
| 2002/0143655 | A1 | 10/2002 | Elston et al. |
| 2003/0050842 | A1 | 3/2003 | Wada et al. |
| 2003/0061074 | A1* | 3/2003 | Dutta et al. ................. 705/4 |
| 2003/0101095 | A1 | 5/2003 | Suzuki |
| 2003/0121929 | A1 | 7/2003 | Liff et al. |
| 2003/0227510 | A1 | 12/2003 | Payne |
| 2004/0148223 | A1 | 7/2004 | Ghaffar et al. |
| 2004/0207868 | A1* | 10/2004 | Lay et al. ................. 358/1.15 |
| 2004/0246287 | A1 | 12/2004 | Usuda |
| 2005/0024682 | A1* | 2/2005 | Hull et al. ................. 358/1.18 |
| 2005/0040230 | A1 | 2/2005 | Swartz et al. |
| 2005/0080651 | A1 | 4/2005 | Morrison et al. |
| 2005/0271446 | A1 | 12/2005 | Minowa |
| 2006/0149587 | A1* | 7/2006 | Hill et al. ................. 705/2 |
| 2007/0045405 | A1 | 3/2007 | Rothschild |
| 2007/0206209 | A1 | 9/2007 | Mount |

OTHER PUBLICATIONS

Jun. 17, 2008, PCT International Search Report PCT/US06/30716.

Jun. 17, 2008, PCT Written Opinion PCT/US06/30716.

Aug. 15, 2007, PCT International Search Report PCT/US06/11843.

Aug. 15, 2007, PCT Written Opinion of the ISA PCT/US06/11843.

Jun. 10, 2009, European Search Report EP 06 78 6463.

Jul. 19, 2007, Claims filed by amendment filed Apr. 7, 2009 in U.S. Appl. No. 11/366,397.

Jun. 7, 2007, Claims allowed by Notice of Allowance mailed Dec. 16, 2009 in U.S. Appl. No. 11/488,126.

Claims filed Jan. 22, 2010 in U.S. Appl. No. 12/692,419.

Jun. 7, 2007, Claims filed by preliminary amendment filed Jun. 3, 2008 in U.S. Appl. No. 11/481,789.

* cited by examiner

600

Prescription Record

| Name of Drug |
| --- |
| Patient Name |
| Doctor ID |
| Date of Prescription |
| Quantity |
| Number of Refills |

Prescription Label Print File

| | |
| --- | --- |
| 701 — Name of Drug | |
| | Patient Name — 705 |
| 710 — Doctor Name | |
| | Drug Expiration Date — 715 |
| 720 — Manufacturer of Drug | |
| | Instructions for Taking Drug — 725 |
| 730 — Quantity in the Package | |
| | Number of Refills — 735 |
| 740 — Date of Fill | |
| | Date Prescription Written — 745 |
| 750 — History/Medical Record Number | |
| | Prescription Number — 755 |
| 760 — Name of Pharmacy | |
| | Address of Pharmacy — 765 |
| 770 — Phone Number of Pharmacy | |
| | Cautions or Warnings — 775 |
| 780 — CID | |
| | Age/DOB — 781 |
| 782 — Gender | |
| | New Prescription — 783 |
| 784 — Refill Number | |
| | Pill Count — 785 |
| 786 — Payer Name (Insurance Company or 'Cash') | |
| | NDC — 787 |

*FIG. 7*

MedGuide Record (220)

| Field | Label |
|---|---|
| 900 | Name of Drug |
| 905 | Important information about the drug |
| 910 | Who should not take the drug |
| 915 | Information a patient should tell a doctor before starting the drug |
| 920 | How a Patient should take the drug |
| 925 | How a Patient should store the drug |
| 930 | What a patient should avoid while taking the drug |
| 935 | The side effects of the drug |
| 940 | Other information about the ailment of which the patient is taking the drugs for |
| 946 | Ingredients of the drug |
| 950 | General information about the safe and effective use of the drug |
| 951 | DCC |

FIG. 9

CHR Content Record (240)

| Field | Label |
|---|---|
| 1000 | CID |
| 1005 | Greeting |
| 1010 | Doctor's Appointment Reminder |
| 1015 | Billing Information |
| 1020 | Promotional Material |
| 1025 | Information Concerning a Related Product |
| 1030 | Discount |
| 1035 | Coupon |
| 1040 | Government Warning |
| 1045 | News Item |

FIG. 10

IMPORTANT NOTE

The following information is intended to supplement, not substitute for, the expertise and judgment of your physician, pharmacist or other healthcare professional. It should not be construed to indicate that use of the drug is safe, appropriate, or effective for you. Consult your healthcare professional before using this drug.

SERTRALINE - ORAL

COMMON BRAND NAME(S)

Zoloft

WARNING

While antidepressants can provide great benefits, a small percentage of children/teenagers taking these medications for various psychiatric conditions have had a worsening of depression/other symptoms, including suicidal thoughts/attempts. However, depression itself can sometimes lead to suicidal thoughts/attempts as well, in both children and adults. Therefore, when medications to treat depression/other psychiatric conditions (antidepressants) are used (especially in children/teenagers) the benefits and risks must be discussed with the doctor. Though there are no similar study results for adults, this warning information applies to adults taking these medications as well.

Tell the doctor immediately if you notice a worsening of depression/other psychiatric symptoms, unusual changes in behavior (including possible suicidal thoughts/attempts) or other mental/mood changes (such as new/worsening anxiety, agitation, panic attacks, trouble sleeping, irritability, hostile/angry feelings, impulsive actions, severe restlessness, very rapid speech). Watch for these symptoms especially at a time of antidepressant dosage change, or when an antidepressant medicine is being started.
USES

Sertraline is a selective serotonin reuptake inhibitor (SSRI) used to treat depression, panic attacks, obsessive compulsive disorders (OCD), post-traumatic stress disorder (PTSD), social anxiety disorder (social phobia), and a severe form of premenstrual syndrome (premenstrual dysphoric disorder or PMDD).

This medication works by helping to restore the balance of certain natural chemicals in the brain.

OTHER USES

This medication has also been used to treat a type of decreased sexual ability (premature ejaculation) in men.

HOW TO USE

FIG. 13

MEDICATION GUIDE
About Using Antidepressants in Children and Teenagers

What is the most important information I should know if my child is being prescribed an antidepressant?

Parents or guardians need to think about 4 important things when their child is prescribed an antidepressant:

1. There is a risk of suicidal thoughts or actions
2. How to try to prevent suicidal thoughts or actions in your child
3. You should watch for certain signs if your child is taking an antidepressant
4. There are benefits and risks when using antidepressants

1. There Is a Risk of Suicidal Thoughts or Actions

Children and teenagers sometimes think about suicide, and many report trying to kill themselves. Antidepressants increase suicidal thoughts and actions in some children and teenagers. But suicidal thoughts and actions can also be caused by depression, a serious medical condition that is commonly treated with antidepressants. Thinking about killing yourself or trying to kill yourself is called *suicidality* or *being suicidal*.

A large study combined the results of 24 different studies of children and teenagers with depression or other illnesses. In these studies, patients took either a placebo (sugar pill) or an antidepressant for 1 to 4 months. *No one committed suicide in these studies*, but some patients became suicidal. On sugar pills, 2 out of every 100 became suicidal. On the antidepressants, 4 out of every 100 patients became suicidal.
For some children and teenagers, the risks of suicidal actions may be especially high.

These include patients with

FIG. 14

PHARMACY NETWORK COMPUTER SYSTEM AND PRINTER

CROSS REFERENCE TO RELATED APPLICATIONS

This application, Ser. No. 11/366,397, claims priority to provisional application 60/759,552, filed Jan. 18, 2006, the contents of which are incorporated herein by reference.

FIELD OF THE INVENTION

This invention relates generally to computerized systems for printing information about medicines sold in pharmacy stores.

BACKGROUND ART

Currently, pharmacy printers print information about a medicine on a medicine label for distribution to the consumer along with the corresponding medicine. Often, the label is designed to be fixed to packaging for the medicine. The medicine label is generated after the consumer orders the medicine and prior to when the consumer receives the medicine. Systems for printing a medicine label and related advisory information are described in U.S. Pat. No. 6,304,849 entitled "Method and system for printing a combination pharmaceutical label and directed newsletter"; U.S. Pat. No. 6,240,394 entitled "Method and apparatus for automatically generating advisory information for pharmacy patients"; and U.S. Pat. No. 6,067,524 "Method and system for automatically generating advisory information for pharmacy patients along with normally transmitted data" all of which name Baxter Byerly as an inventor, and the teachings of which are all incorporated herein by reference.

U.S. Pat. No. 5,729,666 describes conventional processes for generating, in a computer associated with a printer, print files containing font header data enabling the printer to render fonts, and then the computer transmitting the print file to the printer for printing.

A medicine prescription label may include patient name, doctor name, drug expiration date, the name of the drug, the manufacturer of the drug, instructions for taking the drug, the quantity in the bottle, the number of refills, the date of fill, the day the prescription was written, history or medical record number, the prescription number, the name of the pharmacy, the address of the pharmacy, the phone number of the pharmacy, cautions or warnings.

ACRONYMS

NDC is an acronym for National Drug Code.

DCC is an acronym for Drug Classification Code.

CS is used herein as an acronym for "Computer System".

CHR is an acronym for Catalina Health Resources.

POS is an acronym for Point of Sale.

FDA is an acronym for Food and Drug Administration.

CID is an acronym for Consumer IDentification. CID and PID are synonymous in this application.

XML is an acronym for Extensible Markup Language.

DEFINITIONS

A CID means any identifier that can be used to identify a consumer that can be scanned, read, or otherwise entered into a computer.

A "consumer" means a person or family or group of people that use the same CID when purchasing or filling a medicinal prescription in a store, such as a pharmacy store.

A POS is an area where a consumer engages in transactions with a retail store, such as a pharmacy store.

NDCs are codes associated with drugs. Preferably, NDCs are the unique 11-digit 3-segment number that identifies the labeler/vendor, product, and trade package size of a medication listed under Section 510 of the U.S. Federal Food, Drug, and Cosmetic Act.

DCCs are codes associated with medications based upon the medication's effects on human beings such that several medications may have the same DCC.

Individual transaction data includes but is not limited to data conveying some or all of following information: time of transaction, date of transaction, CID, individual transaction ID, pharmacy ID, product purchased, price of product purchases (list price and/or actual price paid), payment instrument type, payment instrument identifier.

Pharmacy, in this application, refers to a retail store in which medicines are provided to consumers.

Database, in this application, means data organized in some format in a computer memory that can be read and written by an associated CS. Such a concept is also referred to as a database management system. Examples of databases include commercial database products such as Microsoft Access, SQL server, and any set of files stored in computer memory that can be accessed by an associated CS.

Network means communication channels (wired or wireless) and protocols that a set of computers can use to exchange and interpret information. Such channels include dial up telephone data connections, private digital corporate network, and the Internet. Such protocols include real connection modem protocols and virtual connection packet protocols like TCP/IP.

A drug monograph is a written description of a drug or medicine associated with an NDC. For example, a monograph can include information such as, introduction, summary, pharmacology, pharmaco-kinetics, FDA approved indications, off-label uses, dosage and administration, adverse effects, overdose, safety data, contraindications, warnings, precautions, drug interactions, efficacy measures, cost comparison, clinical trials, conclusions, recommendations, references, supplied, and research. A drug monogram contains text, which may be stored in a text computer file.

A MedGuide is a guideline containing FDA-approved patient information associated with a DCC. For example, a MedGuide can include information such as, important information a patient should know about the drug, what the drug is, who should not take the drug or medicine, information a patient should tell a doctor before starting the drug, how a patient should take the drug, how a patient should store the drug, what a patient should avoid while taking the drug, the side effects of the drug, other information about the ailment of which the patient is taking the drugs for, the ingredients of the drug, and general information about the safe and effective use of the drug. A MedGuide contains text, which may be stored as a text computer file.

CHR additional content means drug monograph and MedGuide information associated with a medicine.

CHR content means content associated with a patient resulting from applying criteria to the patient's prescription, the patient's master record, or the prescription label print file (defined below).

CHR content may include (1) patient specific information such as, that patient's CID, (2) information concerning products related to a drug which the patient has purchased or for which the patient has received a prescription, or a government warning relating to drugs associated in any way with the patient, (3) information relating to patient health (represented in both text and graphic formats), (4) a news item selected for presentation to the patient, (5) incentive offers for printing in the form of bar coded coupons for discounts off purchase of specified products, or instant discounts applicable against the price or a product in a subsequent purchase by the consumer, typically for health related products, and typically products related to a disease associated with the patient based upon pharmacy product purchase data in the patient's data record.

CHR content may in theory also include, although such inclusion may be prohibited by privacy regulations, the patient's name, address, telephone number, and email address, the patient's doctors appointments reminders, the patient's doctor's name, address, telephone number, and email address, the patient's billing information such as patient's insurance policy identifier.

A prescription label print file herein means a file transmitted to a printer for printing a prescription label for prescription.

A prescription label print job herein means a set of commands to be executed by a printer to print in response to receipt by the printer of a prescription label print file, wherein the prescription label print file does not include CHR content or CHR additional content, but does include a reference to such content, and the prescription label print job include printing of CHR content and CHR additional content referenced by the prescription label print file.

SUMMARY OF THE INVENTION

Objects of the Invention

It is an object of this invention to improved the speed and reliability of information provided to recipients of medicines in pharmacies.

It is another object of the invention to enable centralized control of information to be included by multiple pharmacy stores in medicine labels.

Another object of this invention is to reduce the cost and complexity of systems for generating targeted medicine labels.

SUMMARY OF THE INVENTION

These and other object are generally provided by a network CS that includes a novel printer located in a pharmacy store wherein the novel printer stores a database of one or both of CHR additional content and CHR content, and the printer implements code to enable the printer to selectively incorporate CHR additional content and CHR content in a prescription label print job based upon codes contained in a prescription label print file received by the printer. These and other object are also provided by the network CS that receives prescription order and that determines what CHR content and CHR additional content to include in a prescription label print job for a prescription order and generates and sends to the novel printer a corresponding prescription label print file for the prescription order. Code may exist either on the printer, a central CS, or a local CS that is designed to apply criteria to field values associated with a prescription, such as filed values for fields payor, age/dob, gender, new prescription indicator, refill number, pill count, and NDC to determine what if any CHR content to print in association with the prescription label. The foregoing field values may be incorporated into a prescription label print file received by the printer.

These and other objects are provided by a novel network CS and method of its use wherein the network CS includes at least:

(1) a central CS;
(2) a plurality of local CSs;

wherein said central CS and said plurality of local CSs form a network in which said plurality of local CS and said central CS can communicate with one another via network protocols;

wherein each local CS of said plurality of local CSs is associated with and proximate to one of a corresponding plurality of pharmacy stores, wherein each local CS of said plurality of local CSs includes a CS terminal for inputting information about pharmacy orders and a pharmacy printer for printing information relating to said pharmacy orders;

wherein a first local CS of said plurality of local CSs includes a first pharmacy printer located in a first pharmacy store and a first pharmacy POS located in said first pharmacy store;

wherein said first pharmacy printer includes a first pharmacy printer database storing:

(1) medicine records including in each medicine record a medicine identifier in association with information about the corresponding medicine;

wherein said first pharmacy printer is configured to receive and process print instructions resulting from a pharmacy order containing a specified prescription for a specified medicine having a specified medicine identifier and a specified consumer identifier for a specified consumer, by:

(1) searching in said first pharmacy printer database for information about said specified medicine associated with said specified medicine identifier;

(2) searching in said first pharmacy printer database for additional information to be conveyed to said specified consumer associated with said specified consumer identifier;

(3) printing in association with one another said specified prescription, said information about said specified medicine, and said additional information to be conveyed to said specified consumer.

Optionally, the printer database also includes (2) consumer records including in each consumer record a consumer identifier in association with additional information (referred to herein below as "CHR content") to be conveyed to the consumer associated with said consumer identifier; wherein said first pharmacy printer is configured to (2) search in said first pharmacy printer database for CHR content to be conveyed to said specified consumer associated with said specified consumer identifier and print that CHR content for the consumer in association with said specified prescription.

The association with CHR content or (referred to herein as "CHR content") to be conveyed to the consumer associated with said consumer identifier may be by storing the actual CHR content in the consumer record.

Alternatively, and preferably, the consumer record includes a CHR identifier, and the first pharmacy printer also includes a CHR content or information database containing records having CHR identifiers association with CHR content. In this alternative, the first pharmacy printer includes code to identify, from the CHR identifier in a consumer record, the corresponding CHR content or information for printing for the corresponding pharmacy order.

Preferably, said first local CS includes code instructing said first local CS to transmit to said central CS information about pharmacy orders including associated consumer identifiers and an address associated with said first local CS.

Preferably, the central CS (which may include by definition the CHR CS) includes code for determining from (1) criteria it stores and (2) information about pharmacy orders associated with said specified consumer identification, CHR information to associate with said specified consumer identification, and said CHR CS includes code for transmitting an identifier of said CHR information to associate with said specified consumer identification to said first local CS.

In the preferred embodiment, the central CS and CHR CS are distinct CSs, for example, having different WAN IP addresses, the central CS stores the master patient records and format and transmits prescription label print file to pharmacy printers in response to receipt of prescription order from the local CSs (ASP model), and the CHR CS stores and manages periodic or aperiodic distribution to the local CSs of the CHR content and optionally the CHR additional content (not in response to any particular prescription order).

Preferably, said central CS includes code for transmitting to said first local CS medicine records including in each medicine record a medicine identifier in association with information about the corresponding medicine.

Preferably, said first local CS includes code for storing in said first pharmacy printer database (1) medicine records including in each medicine record a medicine identifier, such as an NDC, in association with CHR additional information about the corresponding medicine, such as a drug monograph and a MedGuide and (2) CHR content information to associate with said specified CID that said first local CS receives from said central CS, such as targeted health information or company sponsored information from the company making the prescribed medicine.

Preferably, said medicine records comprise corresponding drug monograph data and MedGuide data.

Said additional information to associate with consumer identifications may include at least one of (1) names of alternative brands of a medicine specified in prescriptions contained in the corresponding pharmacy order, (2) information and advertising promoting the medicine specified in the prescription or the brand or medicine actually distributed by the pharmacy in response to the prescription (3) an incentive offer for a discount or credit on purchase of a product other than said medicine, (4) health related information broadly targeted based upon available data in the file received by the printer and not specifically promoting any particular product. In addition, the additional information may include sufficient information to imply a patient's disease state, such as a combination of medicines, age, gender, and other information often associated with a specific disease or class of diseases. From that information, an informational message relating to the implied disease state may be triggered and printed for the patient.

In one alternative, said central CS includes code for periodically transmitting additional information that it has associated with said specified consumer identification to said first local CS.

In one alternative, said central CS includes code for automatically transmitting additional information that it has associated with said specified consumer identification to said first local CS in response to transmission from said local CS to said central CS of said specified consumer identification. That enables said additional information to be printed by said first printer concurrently or sequentially with printing by said first pharmacy printer of said specified prescription and information about said specified medicine.

Preferably, the elements of the local CS including the CS terminal and the pharmacy printer in each pharmacy store are inside a local area network (LAN).

Preferably, the central CS is networked to each one of the local CSs over a wide area network, such as a private WAN, the Internet, or a set of dial up Plain Old Telephones (POTs) lines. Preferably, the data transmission speed in said LAN is greater than the data transmission speed in said WAN.

The inventors recognize that, while drug monographs and MedGuides can be stored as relatively small text files, the graphical information for CHR content that the inventors want to associate with CIDs may require a relatively large amount of memory for storage, often occupying more than one megabyte and typically occupying on the order of 10 megabytes. The inventors envision the size of data storing this information to increase with time, for example, possibly to 100 megabytes in the next few years. The inventors envision storing much or all of this CHR content data locally in the pharmacy printer, thereby avoiding redundant data transfer to the pharmacy printer of large volumes of CHR content.

The printer may also store local rules that the printer implements in addition to the rules instructing it what to print based upon identifications of medicines and CIDs. The additional local rules may instruct the printer with (1) additional content local rules, to print additional text or graphics, upon receipt of instructions to print specified CHR content and/or additional CHR content and the other print file information, and with (2) layout local rules, to lay out all of the material for printing defined by the print file information and the specified CHR content and/or additional CHR content, depending upon all of the material for printing, the type of the local printer, and local printer's print specifications, such as paper width and margins. Preferably, one or both of the central CS and the CHR CS store a master set of rules based upon printer type, material for printing, and print specifications, and includes code specifying that the central CS or CHR CS distribute corresponding rules to printers having the printer type, material for printing, or print specifications stored by the central or CHR CS, or both.

The first pharmacy printer may receive in response to a single pharmacy order print instructions from a first local CS controller CPU in the first local CS and also from the central CS. For example, the first local CS controller CPU may process the pharmacy order payment aspects to specify costs of the transaction, to itemize product items included in the pharmacy order, to request and receive payment or credit from a third party insurer or credit card company. The central CS may receive at least the prescription information in the pharmacy order and respond during the transaction involving a consumer in the first pharmacy by transmitting CHR additional content identifiers in association with the prescription and an order ID, or in association with the CID, back to the first pharmacy printer. The central CS may associate the customer master record with the prescription order and transmit back to the local CS a prescription record supplemented by information from the customer master record, and that transmission may include or contain the prescription label print file for the prescription. The first pharmacy printer may include code to prioritize print instructions received from both the first local CS controller CPU and the central CS regarding a single pharmacy order, and print transaction information, prescription label, and all other related information accordingly.

The pharmacy printer may be configured to print partially on an adhesive backed portion of printer paper and partially on a non-adhesive backed portion of paper. For example, the pharmacy printer may be designed to format printing so that prescription information is printed on an adhesive backed portion so that it can be readily attached to a prescription drug container, and the pharmacy printer may be designed to format printing so that CHR additional content (drug monograph, MedGuide), and CHR content is printed on a portion of material having a perforation separating it from the prescription information so that it can be separated at a perforation line from the prescription label portion of the pharmacy label.

The central CS may store transaction data it receives from each one of the plurality of local CSs. The central CS may run criteria against all transaction data associated with a CID, regardless at which pharmacy stores the transaction data originated.

Preferably, the CHR CS maintains an up to date list of drug monograph and MedGuide data for a large number of drugs, and updates each of the pharmacy printers with that information via transmissions over the network. Alternatively, or in addition, the central CS, may also CS maintain an up to date list of drug monograph and MedGuide data.

In some embodiments, the local CSs only transmit, outside of its LAN, de-identified pharmacy order information and encrypted versions of the associated CIDs to protect privacy. De-identified, means that information that could be used to identify the corresponding person, is removed. That information includes for example, name, residence address, telephone number, email address, and demographic information particular to a small group of individuals. Either the CHR CS or the central CS may run criteria on the de-identified information and transmit back to the local CS encrypted CIDs in association with identifiers for CHR information, and the pharmacy printer includes code to associate those from the encrypted CID, the non-encrypted CID. Preferably, the CHR CS runs the foregoing criteria.

The local CS may be implemented in various network architectures. For example, the local CS may be a POS CS that includes a store controller CPU having a LAN address, a pharmacy printer including a CPU and memory and also having a LAN address, and a router logically separating the LAN from the WAN. Alternatively, the store controller CPU may act as a router logically separating the LAN from the WAN. Alternatively, the pharmacy printer may include a CPU and memory but have no separate LAN address, and instead it may communicate with the store controller CPU via always on connections as opposed to packet switched virtual connections.

Examples of criteria that can be used to determine CHR content to associate with a CID or encrypted CID include: NDC, age; gender; number of allowed refills; refill number; payor; whether the prescription is a new prescription; implied patient disease state; no criteria (associating certain CHR content with every CID, such as public announcements); sequential (distribute certain additional CHR content to every second, third, fourth, etc. CID identifier from a POS, as they appear at a POS, or as they appear in a local CS having multiple POSs); random (randomly distribute certain CHR content to CIDs); to specified frequent shoppers based upon shopping or specific product purchase frequency or existence of a prior purchase, specified demographic data, specified frequency of purchases, specified frequency of visits to a location, specified frequency that a consumer exercises incentives, specified purchase history of the consumer, specified particular circumstances in the consumer's life, specified indicated tastes of the consumer, other characteristics of the consumer associated data that indicates a consumer possesses certain traits, specified purchase of specified items in specified time periods, specified transaction dollar volume, specified transaction frequency, specified associated pharmacy, region, address, retail chain, and/or postal code.

Preferably, a patient master record table exists, either stored locally in local CS database 30A or centrally in central CS database 20A or CHR CS database 50A, or stored at any combinations of the foregoing. Preferably, the patient master record table includes for each record fields storing for example: CID or encrypted CID, date of birth or age, gender, insurance plan ID, payor, and insurance company name. The patent master record may be used to associate date of birth or age, gender, insurance plan ID, payor, and insurance company name with a patient's prescription record, and to determine CHR non-CID additional content mentioned below.

Example of CHR content triggered by those criteria include (1) additional information provided by the company producing that medicine about a prescribed medicine, and information about a disease which can be associated with the patient based upon data in the customer master record table, or, associated with the patient by the printer based upon the data it receives in the prescription label print file.

BRIEF DESCRIPTION OF DRAWINGS

FIG. 6 shows data elements of a prescription record 600 received from terminal 30C of local CS 30;

FIG. 7 shows data elements that may be in a data transmission of a prescription label print file to pharmacy printer 40 in response to a pharmacy order received from terminal 30C of local CS 30;

FIG. 9 shows data elements in MedGuide table 220 of FIG. 2;

FIG. 10 shows data elements in CHR content table 240 of FIG. 2;

FIG. 13 is the first page of a drug monograph for the drug brand name Zoloft; and FIG. 14 is the first page of a MedGuide for the drug corresponding to brand name Zoloft.

DETAILED DESCRIPTION OF THE INVENTION

Figure 1:
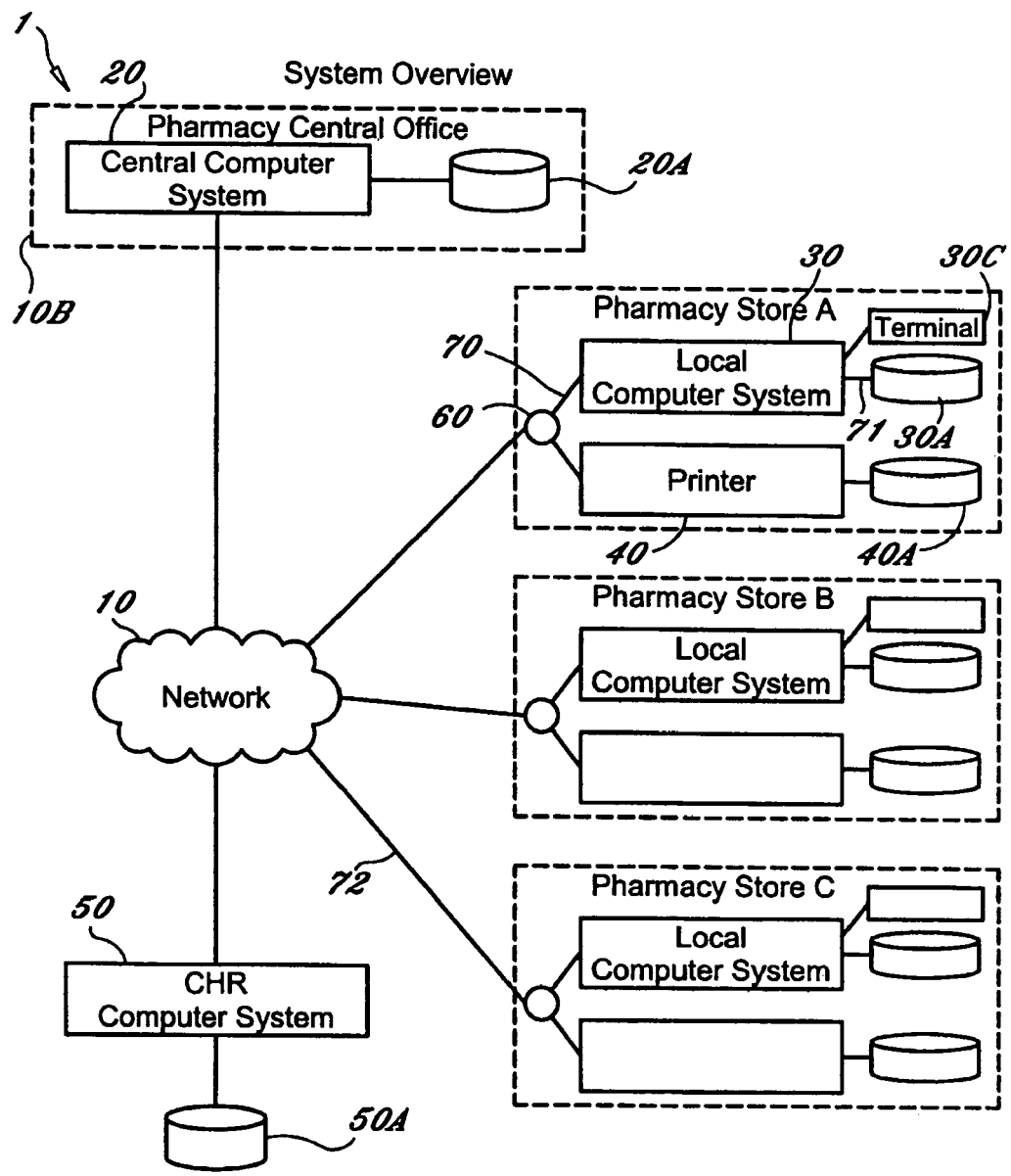
FIG. 1 is a schematic of a novel network CS.

FIG. 1 shows novel network CS 1 including:
WAN network 10;
associated with a pharmacy central office: central CS 20; and a central CS database 20A;
associated with pharmacy store A,30: local CS 30; local CS database 30A; local CS terminal 30C; pharmacy printer 40; pharmacy printer database 40A; pharmacy store switch 60;

pharmacy stores B, C, . . . indicating equivalent network computer structure to that illustrated for pharmacy store A;

CHR CS 50 and CHR CS database 50A; and line 70, 71, 72.

Network 10 may be the Internet, a private packet switching network, or a telephone dial up communication system. Lines 70 represent local area network (LAN) connections between network addressable computerized components. Lines 71 between a CS and a database represent that the connected CS controls read and write access to the connected database. Lines 72 between computer components and WAN 10 represent a relatively slow speed network connection to WAN 10.

Each one of central CS 20, local CS 30, and CHR CS 50 includes a digital central processing unit, human user input and output devices, and associated high speed memory. Each one of these CSs stores network protocols and code for converting and transmitting data in those network protocols, such as TCP/IP.

One or both of local CS 30 and central CS 20 are configured to receive and store in their respective databases pharmacy transaction data for transactions in pharmacy store A.

Pharmacy store switch 60 in a preferred embodiment is a router designed to route packet switched signals from computers inside a LAN, such as a LAN including local CS 30 and printer 40, to WAN IP addresses, such as an address for central CS 20, and to route packets from the WAN to the associated LAN computers specified by IP address information in incoming packets.

In one less preferred alternative embodiment, store switch 60 is replaced by a dial up modem telephone connection.

In another less preferred embodiment, no pharmacy store switch 60 exists and network addressing services to both printer 40 and local CS 30 are provided local CS 30. In this alternative, all signals addressed to printer 40 first pass through local CS 30.

Printer 40 includes conventional structure or code for printing based upon print instructions, and also conventional structure or code for receiving and interpreting information in at least one network protocols, such as TCP/IP.

In preferred embodiments, printer 40 also includes in printer database 40A drug monograph, MedGuide, and CHR additional content, along with a list of pointers to data elements therein. In these preferred embodiments, printer 40 includes structure or code for acting on instructions including pointers and/or names data, for including in a pharmacy label printout, monograph, MedGuide, and CHR additional content identified by the pointers and names.

CHR CS 50 and its database 50A store addresses of CSs to update with drug monograph, MedGuide, and CHR content, addresses and/or names for each drug and content's data record, criteria for selecting drug monograph, MedGuide, and CHR content, code to distribute updated content, address, and name information to CSs.

Central CS 20 and database 20A optionally includes therein all data and function ascribe to CHR CS 50.

Central CS 20 runs code implementing criteria on pharmacy transaction data associated with CIDs to determine specified content to associate with the CIDs. Central CS 20 distributes identifiers of specified content associated with an associated CID, in association with that CID, back to the pharmacy printer or printers from which the transaction data originated. The transmission may be to an address for each such printer. Alternatively the transmission may be to an address for a local CS containing that printer in which case the local CS is programmed to forward the transmission or at least the identifiers and associated CIDs to the pharmacy printer.

For example, criteria may depend upon patient age, gender, prescription history, or product purchase history. Specific content associated via criteria with a CID may include informational messages, incentive offers to purchase or sample a product, and instant discounts.

Tables herein means both tables as defined for relational database structures and other data associations such as those enabled by XML and XML tagging.

Figure 2:
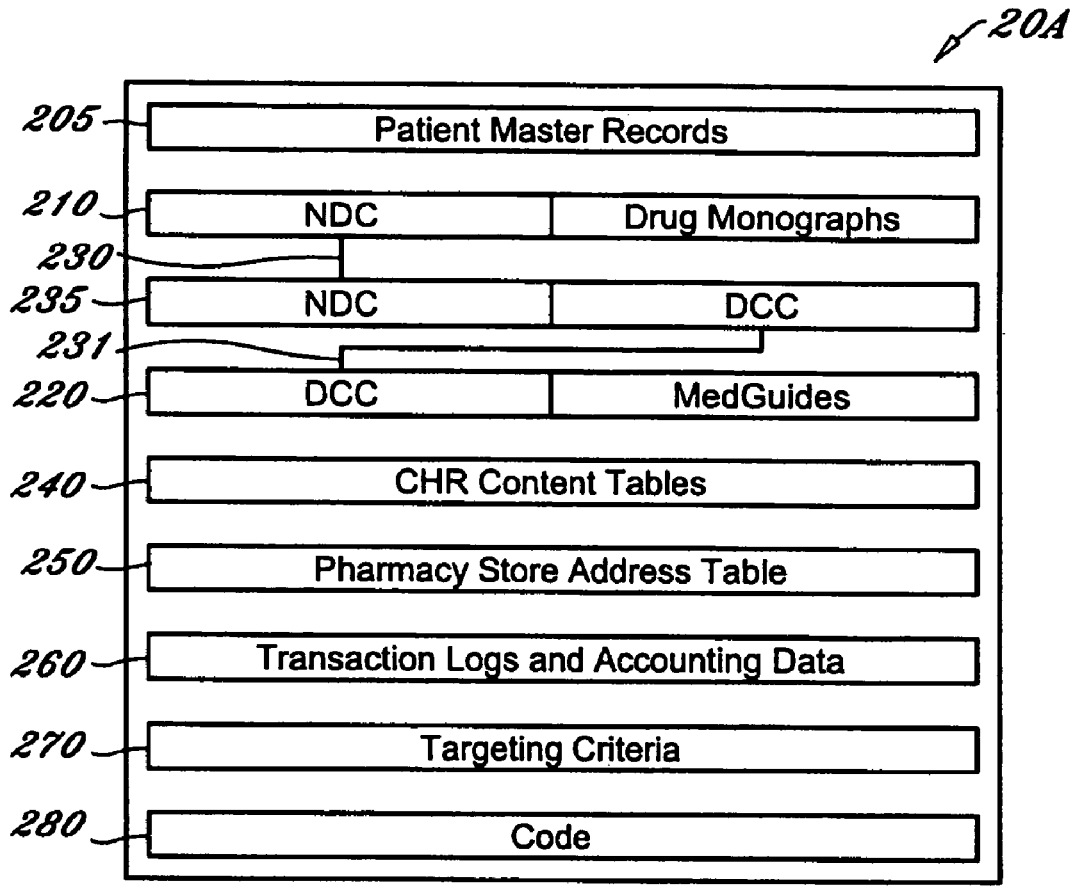
FIG. 2 is a schematic of a data structure of central CS database 20A of FIG. 1.

FIG. 2 shows central CS database 20A of FIG. 1 as including patient master records table 205, drug monograph table 210, MedGuide table 220, NDC/DCC association table 235, link 230 from NDC field of drug monograph table 230 to NDC/DCC association table 235, link 231 from DCC field of NDC/DCC table 235 to DCC field of MedGuide table 220, CHR content table 240, pharmacy store addresses table 250, transaction logs and accounting data structure 260, targeting criteria data structure 270, and code 280. As mentioned above, central CS database 20A may also include the CHR content table 240 shown in FIG. 5. Links 230, 231 denote that data fields in records for drug monographs and MedGuide information store corresponding data to field in the NDC/DCC table. Links 230, 231 enable code to determine which drug monographs correspond to MedGuides for that drug.

Central CS 20 uses pharmacy store address table 250 to store network addresses data for local CSs and pharmacy store printers. A CHR CS may store an analogous table. Central CS 20 uses data structure 260 to store transaction logs and accounting logs based upon data received from the plurality of local CSs. In some cases, transaction logs data contain encrypted CIDs and de-identified transaction data.

Preferably, central CS 20 received complete data transaction records and any CHR CS received de-identified records.

Code 280 includes for example operating system code, and applications code, including the code to transmit content, identifiers in association with CIDs, to determine network addresses for transmissions, and to determine associations of content identifiers with CIDs.

Figure 3:
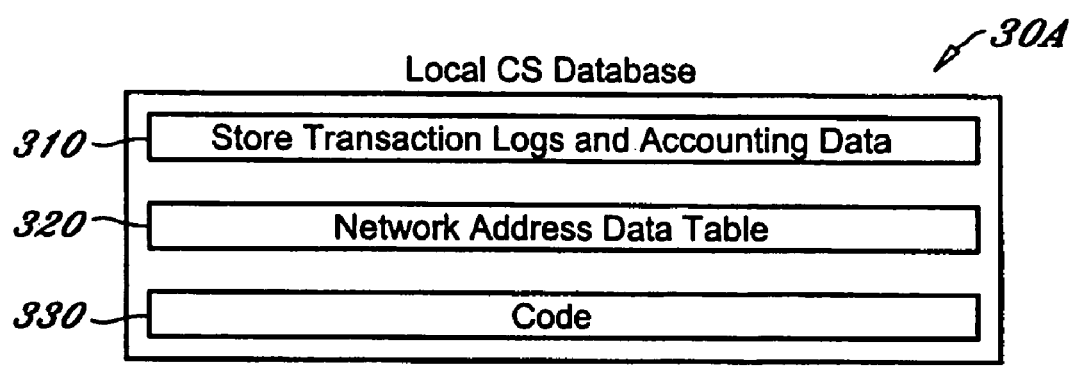
FIG. 3 is a schematic of a data structure of local CS database 30A of FIG. 1.

FIG. 3 shows local CS database 30A preferably including store transaction logs and accounting data structure 310 for storing transaction logs and accounting data for the corresponding pharmacy store, network address and data table 320 for storing for example LAN and WAN network addresses, and code 330.

Code 330 could include for example aspects of conventional local POS CS processing for accounting for inventory and transactions.

Figure 4:
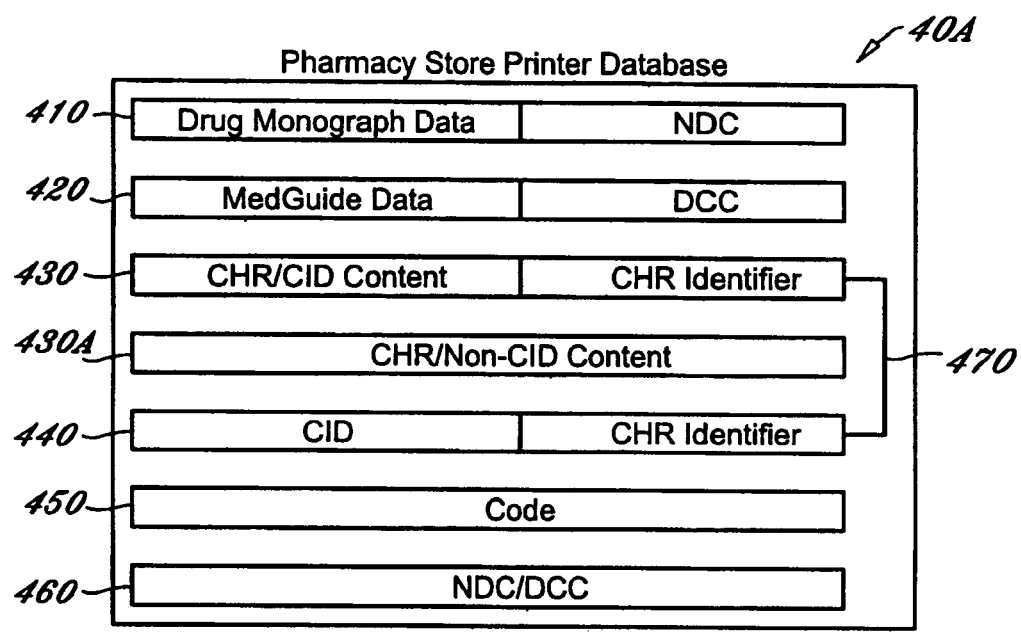
FIG. 4 is a schematic of a data structure of pharmacy store printer database 40A of FIG. 1.

FIG. 4 shows pharmacy store printer database 40A including drug monograph table 410, MedGuide table 420, CHR/CID content table 430, CID/CHR identifier table 440, CHR/Non CID content table 430A, identifier table 440 code 450, NDC/CDD table 460, and logical association line 470. Tables 410 and 420 are segmented to illustrate the NDC or DCC identifiers for corresponding data describing a specified drug or class of drugs. CHR content table 430 is likewise segmented to show that it contains a CHR identifier field. Table 440 is likewise segmented to show that it contains both CID and CHR identifier fields. The lines 460, 470 define fields containing the information. Table 460 indicate that drug monograph and MedGuide information for the same medicine can be matched, and that CHR content may be associated with a CID via the matching of CHR identifiers. The existence of the NDC field, the MedGuide field, and the CID field enable the printer to receive drug name data and CID data and to determine from that data drug monograph and MedGuide information to print, and to determine CHR content to print, in association with a prescription label for a prescription for a patient having that CID.

CHR/non CID additional content table 430A includes field for NDC, whether prescription is new, number of refills remaining, number of refills used, payor, pill count or quantity, gender, age and or date of birth, and associated informational content. CHR/non CID additional content table 430A does not include a CID field. Printer 40 uses this data to determine from data in a prescription label print file whether to include in the prescription label print job associated informational content. It does so by implementing code matching values and ranges of these fields to records in table 430A. For example, printer 40 may run code determining whether a prescription label print file table 430A is for a male over age 50 having an insurance payor and, if so, printing, along with the patient's prescription label, information about Viagra, which is a male oriented drug suitable for older men, and if not, not printing out the information about Viagra. The matching is not dependent upon CID.

The code and determination whether to print based upon the fields whether prescription is new, number of refills remaining, number of refills used, payor, pill count or quantity, gender, age and or date of birth may occur at the central CS or the CHR CS, be associated with a CID, and then be transmitted as a CHR/CID content record to the pharmacy printer database CHR/CID content table 430, to await the pharmacy printer's identification of that CID in a prescription label print file or when the patient's CID is identified in a transaction in the pharmacy. Thus, the non-CID targeting determinations for CHR content may either occur remote from the local CS at any time or locally in the local CS and preferably in the pharmacy printer using the pharmacy printer database in response to and as part of processing of receipt of a prescription label print file into a prescription label print job for printing by the pharmacy printer.

Figure 5:
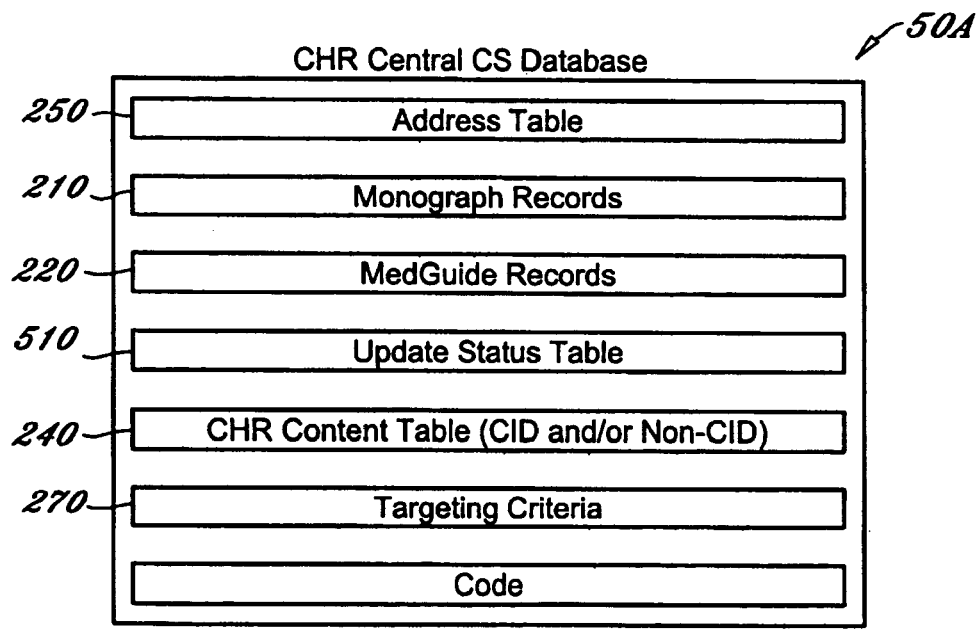
FIG. 5 is a schematic of a data structure of CHR CS database 50A of FIG. 1.

FIG. 5 shows database 50A of optional additional CHR CS as including substantially the same data structures as central CS database 20A, and also including update status table 510 to indicate the status of monograph, MedGuide, and CHR content of each one of the local CSs and/or pharmacy printers. Central CS 20 may use the update information to determine when to send new data sets of information to the various local CS and pharmacy printer databases.

FIG. 6 shows data elements of a prescription record 600 received from terminal 30C of local CS 30 including fields for name of drug, patient name, doctor ID, date of prescription, quantity, number of refills. In this regard, the terminal may be one at which a clerk manually keys in the prescription information, or it may be an automated system to receive and process prescriptions transmitted remotely from outside the pharmacy store to the pharmacy store's local CS, such as via web access, email, or automated telephone service. Either the local CS or the central CS may associate with that information a CID, associate with a de-identified subset of that information an encrypted CID, and determine from the CID or encrypted CID, additional information relating to the prescription and the customer as noted in the prescription record 700 in FIG. 7. The local computer system may transmit in de-identified form the prescription information and/or product purchase transactions, to the CHR CS.

FIG. 7 shows a data record for a prescription of the type to be transmitted (either from central CS 20 or local CS 30) to pharmacy printer 40 in response to a pharmacy order received from terminal 30C. The field or tag names may include name of drug 701 field; patient name 705 field; doctor name 710 field; drug expiration date 715 field; manufacturer of drug 720 field; instructions for taking drug 725 field; quantity in the package 730 field; number of refills 735 field; date of fill 740 field; date prescription was written 745 field; history/medical record number field 750; prescription number field 755; name of pharmacy field 760; address of pharmacy 765 field; phone number of pharmacy 770 field; cautions or warnings 775 field; and CID 780 field; Age/DOB 781 field; gender 782 field; whether a new prescription 783; refill number 784 field; pill count 785 field; payor name 786 field; and NDC 787 field.

Name of drug 700 field stores the name of the drug for which the prescription was written.

A complete list of the currently contemplated fields in the data record for a prescription of the type to be transmitted) to pharmacy printer 40 include, in XML tagged data format: message version number; state code for store location; geographic region; division ID to aid in triggering division specific programs; store ID to aid in triggering store specific programs; national council for prescription provider ID; English or Spanish language preference; pharmacy system's unique patient identifier; customer name; name mask flag field indicating printing "Valued Customer" instead of patient name; date of birth; gender; opt out flag indicating patient does not want information based upon patient's record; transaction sequence number generated by local CS for Q/A purposes; script status indicating whether prescription is a new unfilled prescription or a refill; NDC; medication name; prescription number printed on newsletter; dispensed quantity of medication (pill count); daily supply quantity; number of days supply; original fill date; expiration of prescription date; prescription refills remaining; alpha numeric associated with a drug monograph; patient directions; doctor's ID; pharmacists directions; boolean indicating whether printing of prescription and newsletter are simplex or integrated; boolean indicating whether to print HIPAA notice; payor (third party payor name or "CASH" if paid by customer); payor code (third party payor code or "CASH" if paid by customer); payor's processor control number; bank identification number; legal relationship between agent and principal for the prescription; insurance policy group ID; and insurance policy plan ID. Based upon any of the foregoing data fields having data possibly transmitted to the printer, the following data fields and combination of fields are contemplated with boolean combinations of rules for triggering to provide different information to different patients:

ndc
ndc/age/gender
ndc/refill
ndc/new
ndc/PillCount
ndc/refill#
ndc/refills remaining
age/gender
payor
payor/ndc
payor/age/gender
payor/ndc/age/gender
payor/ndc/refill
payor/ndc/new
patient ID or CID
Ndc/patient
Ndc/new/patient
Ndc/refill/patient
Ndc/refill#/patient
Ndc/age/gender/refill/new
Ndc/bin no
Refill/new/patient ID In one preferred embodiment, the printer receives the prescription label print file as an XML data stream, and data for the foregoing currently contemplated fields exists and the beginning of the data stream between XML tags indicating to in the PCL printer language to ignore the tagged contents, such as between "1Bh&foX" and "27d&f1X" tags.

An example of a sample prescription label and CHR content file layout is as follows.
Sample Label Stream Layout
Printer PCL*
[esc]E[esc]&12S[esc]&11H[esc]&11o
CHR tagged info
[esc]&f0X[All CHR non-print data elements here][esc]&f1X
Pharmacy back side data
[monograph]
CHR back side marker
[esc]&f0X[esc]&f1X
Pharmacy front side data1
[label information]
CHR front side marker
[esc]&f0X[esc]&f1X
Printer reset
[esc]E An example of an XML string passing CHR information is as follows:
esc&f0X
<newsletter>
<BinNumber>12</BinNumber>
<ControlNumber>12313</ControlNumber>
<DailySupply>2</DailySupply>
<DaysSupply>30</DaysSupply>
<DateOfBirth>02/01/1952</DateOfBirth>
<DispQty>100</DispQty>
<DrDEA>12323</DrDEA>
<Gender>M</Gender>
<HIPAA>Y</HIPAA>
<Language>E</Language>
<MaskName>N</MaskName>
<MedicationName>DuraVent D/A</MedicationName>
<NCPDP>123</NCPDP>
<NDC>12345678901</NDC>
<OptOut>N</OptOut>
<PatientID>123456</PatientID>
<PatientName>Joe Public</PatientName>
<Payor>CASH</Payor>
<RefillsRemaining>2</RefillsRemaining>
<ScriptStatus>N</ScriptStatus>
</newsletter>
esc&f1X
Note: The above information is intended as an example and not all fields are included.

Patient name 705 field stores the name of the patient for which the prescription was written. Optionally, this data field may be added to record 700 in printer 40 in response to receipt of a CID or encrypted CID.

Doctor name 710 field stores the name of the doctor who wrote the prescription for the patient.

Drug expiration date 715 field stores the date in which the drugs will expire.

Manufacturer of drug 720 field stores the name of the manufacturer of the drug.

Instructions for taking drug 725 field stores instructions for taking the drug. Such instructions can include: take only at night, take 3 pills a day, take with a full glass of water, or the like.

Quantity in the package 730 field stores how much of the drug was given the to the patient. For example, this field could store that 32 pills were given to the patient, or 12 oz., etc.

Number of refills 735 field includes how many times the patient may refill the prescription without needing a new prescription from the doctor. For example, this field could store the number 6, indicating that the prescription may be refilled 6 times.

Date of fill 740 field stores the date in which the prescription was filled.

Date prescription was written 745 field stores the date that the prescription was written.

History/medical record number 750 field stores a medical number unique to the patient.

Prescription number 755 field stores a unique number designated by the pharmacy that filled the prescription.

Name of pharmacy 760 field stores the name of the pharmacy which filled the prescription.

Address of pharmacy 765 field stores the address of the pharmacy which filled the prescription. Such address can include a website address or a street address, including street, city, state, and zip code.

Phone number of pharmacy 770 field stores the phone number of the pharmacy.

Cautions/warnings 775 field stores any cautions or warnings issued by the government, pharmacy, or doctor in taking the drug. For example, the label could read: Caution: Federal law prohibits transfer of this drug to any other person than patient for whom prescribed.

CID 780 field stores a CID. Optionally, the field may be added by printer 40 in response to receipt of and decryption of an encrypted CID.

Age/DOB field 781 stores age in year or date of birth of the patient.

Gender field 782 store gender, either male or female, or status unknown.

New prescription field 783 store a boolean value indicating whether the prescription is for an unfilled new or a refill request.

Refill number field 784 indicates the number of fills the patient has obtained on the prescription.

Pill count field 785 indicated the number of pills or quantity of non-pill medicine specified in the prescription.

Payor name field 786 indicated the name of the health insurance company payor if one exists, or "cash" if no the customer does not have or use a health insurance policy.

NDC field 787 stores the NDC number for the medicine provided.

Figure 8:
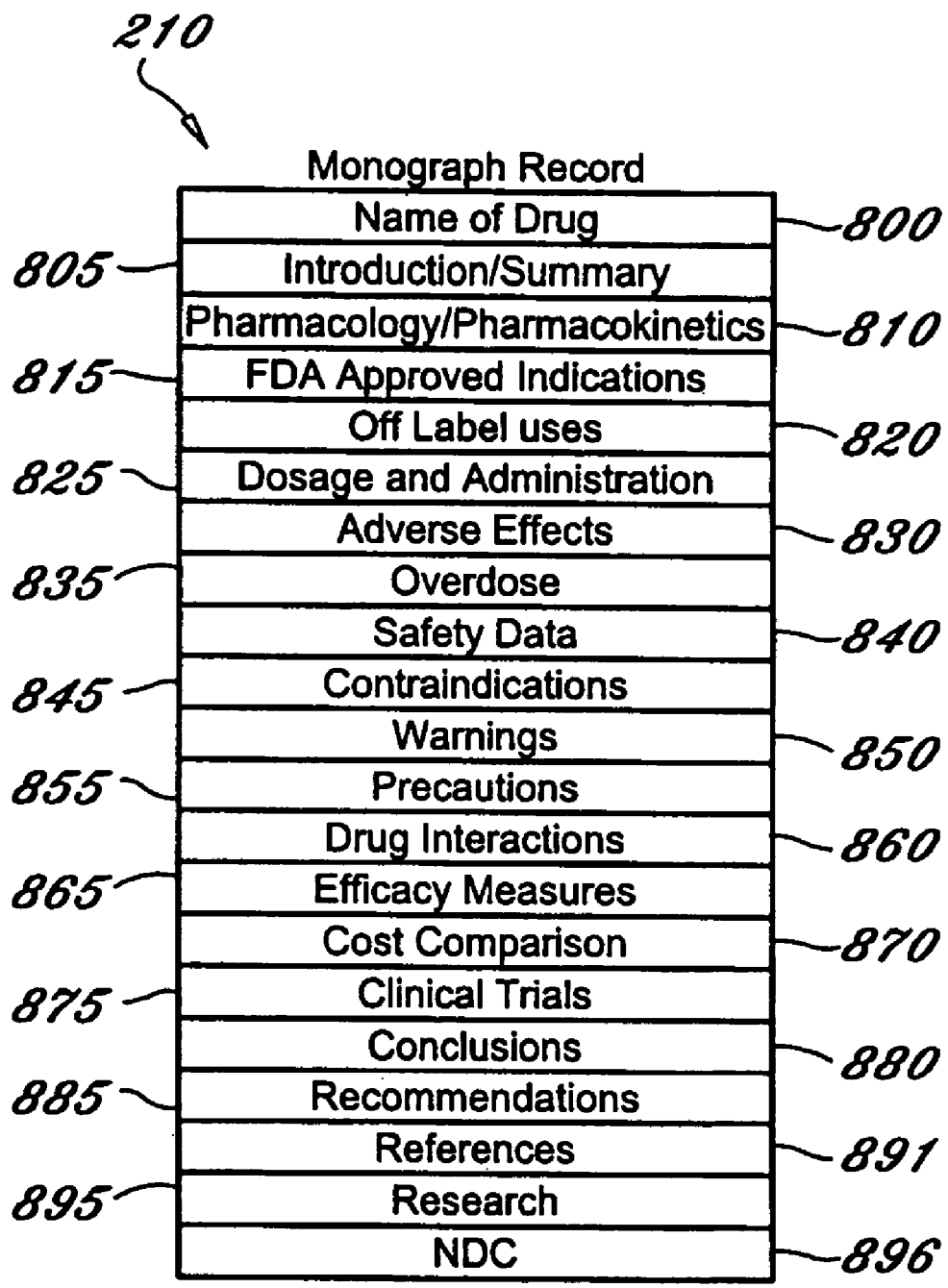
FIG. 8 shows data elements in a drug monograph record 210.

FIG. 8 shows a representation of a monograph record in which monograph record preferably includes name of drug field 800; introduction/summary 805; pharmacology/pharmacokinetics field 810; FDA approved indications field 815; off label uses field 820; dosage and administration field 825; adverse effects field 830; overdose field 835; safety data field 840; contraindications field 845; warnings field 850; precautions field 855; drug interactions field 860; efficacy measures field 865; cost comparison field 870; clinical trials field 875; conclusions field 880; recommendations field 885; references field 890; research field 895; and NDC field 896.

Name of drug 800 field stores the name of the drug.

Introduction/summary 805 field stores a summary of the information provided in the monograph.

Pharmacology/pharmacokinetics 810 field stores the composition of the drug, its uses, effects, the characteristics or properties of the drug that make it medically effective, the process by which the drug is absorbed, distributed, metabolized, and eliminated by the body.

FDA approved indications 815 field stores symptoms or particular circumstances that indicates the advisability or necessity of a specific medical treatment or procedure.

Off label uses 820 field stores uses relating to the drug to treat a condition which has not been approved by the FDA.

Dosage and administration 825 field stores the amount of the drug that should be taken and when it should be taken. This field may store different dosage amounts depending on an individuals situation, such as age, or what they are taking the medicine for.

Adverse effects 830 field stores the adverse effects of the drug. For example, adverse effects can include one or more of: headache, nervousness, insomnia, drowsiness, fatigue or asthenia, anxiety, tremor, dizziness, lightheadedness, nausea, diarrhea, and excessive sweating.

Overdose 835 field stores information about how much of the drug is considered overdose, if and how a person has died from overdose, symptoms of overdose and treatment.

Safety data 840 field stores safety data on the drug, such as data regarding safety in humans, in animals, and in vitro studies.

Contraindications 845 field stores factors that render the administration of the drug inadvisable.

Warnings 850 field stores information such as allergic reactions, who should not take the drug, what may happen to people who take the drug that should not be, and what may happen to a person if they overdose.

Precautions 855 field stores information with advice of what to do in advance to protect against possible danger, failure, or injury related to the drug.

Drug interactions 860 field stores information about reactions with other drugs or food interaction with the prescribed drug.

Efficacy measures 865 field stores the ability of the drug to control or cure an illness.

Cost comparison 870 field stores a table which compares similar drugs and dosages and their associated costs.

Clinical trials 875 field stores data on the clinical trials, such as the method, the criteria, results, conclusions, and critiques.

Conclusions 880 field stores the conclusions of the monograph.

Recommendations 885 field stores how the drug will be available, such as an open access basis or whether the drug should be made available.

References 890 field stores a list of references cited to in the monograph.

Research 895 field stores the research data that was analyzed to arrive at the present monograph.

NDC field 896 stores the NDC for the named drug.

FIG. 9 is a representation of one alternative for a MedGuide record which may include name of drug 900 field, important information about the drug field 905; who should not take the drug field 910; information a patient should tell a doctor before starting the drug field 915; how a patient should take the drug field 920; how a patient should store the drug field 925; what a patient should avoid while taking the drug field 930; the side effects of the drug field 935; other information about the ailment for which the patient is taking the drugs for field 990; ingredients of the drug field 995; general information about the safe and effective use of the drug field 950; and DCC for the drug field 951.

Name of drug 900 field stores the name of a drug.

Important information about the drug 905 field stores a summary of what the drug is used to treat, severe side affects, and other important information.

Who should not take the drug 910 field stores information regarding who should not take the drug; such as, a person allergic to an ingredient in the drug should not take the drug.

Information a patient should tell a doctor before starting the drug 915 field stores information regarding what a doctor should know before prescribing the drug. Such information can include, whether the patient is pregnant, medical history, other drugs the patient is taking, allergies, and the like.

How a patient should take the drug 920 field stores information on how the drug should be taken. For example, the field can store the information that the drug should be taken in tablet form orally every 4 hours.

How a patient should store the drug 925 field stores information about storing the drug. This field can contain information such as, store at room temperature in a closed container, away from heat, moisture, direct light, or keep away from children.

What a patient should avoid while taking the drug 930 field stores information about what a patient should avoid while taking the drug, such as, alcohol or other medications.

The side effects of the drug 935 field stores information on side effects of the drug; such as, drowsiness, headaches, nausea, dizziness, etc.

Other information about the ailment of which the patient is taking the drugs for 940 field stores other information about the ailment such as what else is used to treat it, the history of the ailment, and characteristics of patients who have the ailment.

Ingredients of the drug 945 field stores the ingredients of the drug.

General information about the safe and effective use of the drug 950 field stores general information about the safe and effective use of the drug.

Alternatively, all information for each MedGuide may be stored in a single text or image field in association with a DCC for the named drug.

FIG. 10 shows a representation of a CHR content record which may include for example a CID 1000 field, a greeting 1005 field, a doctor's appointment reminder 1010 field, billing information 1015 field, promotion material 1020 field, information concerning a related product 1025 field, discount 1030 field, coupon 1035 field, government warning 1040 field, and news item 1045 field.

CID 1000 field stores a CID. Optionally, this field may be generated in printer 40 upon receipt of an encrypted CID.

Greeting 1005 field stores a greeting for the consumer.

Doctor's appointment reminder 1010 field stores a reminder for a consumers doctor's appointment. This field may not be present in implementations employing encrypted CIDs and de-identified information.

Billing information 1015 field stores information regarding billing, such as who was billed, how much the bill was, who paid for the bill, and the like.

Promotion material 1020 field stores information promotion drugs consumer is on, related drugs, new drugs, etc.

Information concerning a related product 1025 field stores information concerning a related product.

Discount 1030 field stores discounts for drugs consumer is taking, related drugs, new drugs, etc.

Coupon 1035 field stores coupons for drugs consumer is taking, related drugs, new drugs, etc.

Government warning 1040 field stores warnings issued by the government with respect to the drug or ailment.

News item 1045 field stores news information about the drug, a related drug, or any medical news.

Figure 11:
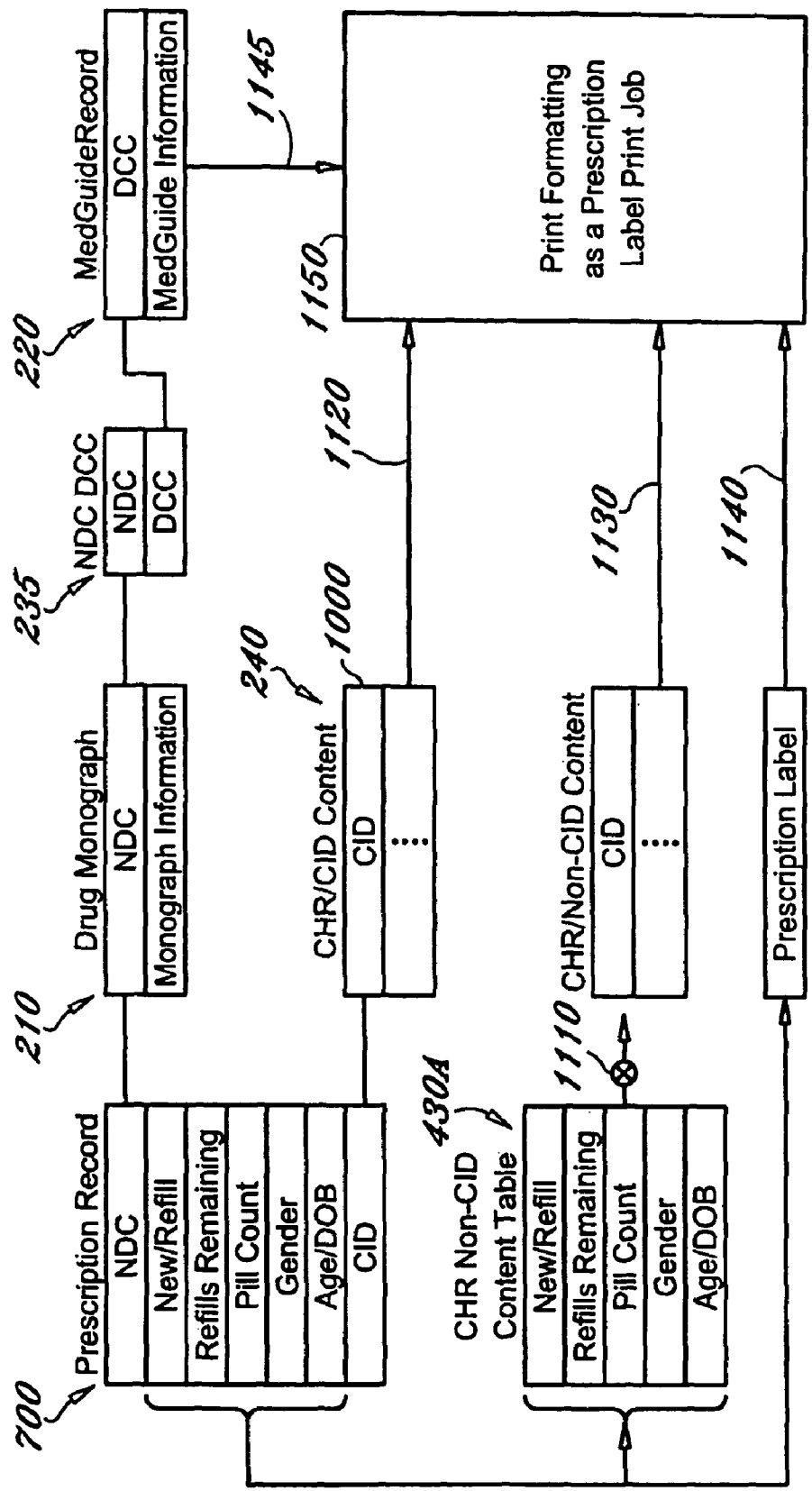
FIG. 11 is a schematic showing inter relationships between elements of the drug monograph, MedGuide, and CHR content records and process flow for printing prescription labels with drug monograph, MedGuide, and CHR information.

FIG. 11 shows exemplary relationships between table or corresponding data elements in the various data record types including prescription record 700, drug monograph table 210, MedGuide record NDC/DCC table 235, CHR/CID additional content 240, and CHR non-CID additional content table 430A leading to printing.

FIG. 11 shows prescription record table 700 logically linked to drug monograph table 210 via NDC code. FIG. 11 shows Drug Monograph table 210 logically linked to MedGuide record 220 via correspondence of NDC to DCC in NDC/DCC lookup table 235. FIG. 11 shows identification of pre-existing stored CHR/CID additional content record 240 for CID in prescription record 700 via identification in prescription record 700 of a corresponding CID.

FIG. 11 shows CHR non-CID additional content table or filter 430A and corresponding fields in prescription drug record 700 for new/refill, refills remaining, pill count, gender, and age/DOB. Printer code determines which if any records in table 430A have values matching the corresponding field values in prescription record 700, as indicated by operator 1110. FIG. 11 schematically shows data flows 1120, 1130, 1140, 1145 of data for CHR/CID content, CHR non-CID content, CHR additional content (drug monograph and MedGuide), and prescription label content for formatting 1150 as a prescription label print job.

Figure 12:
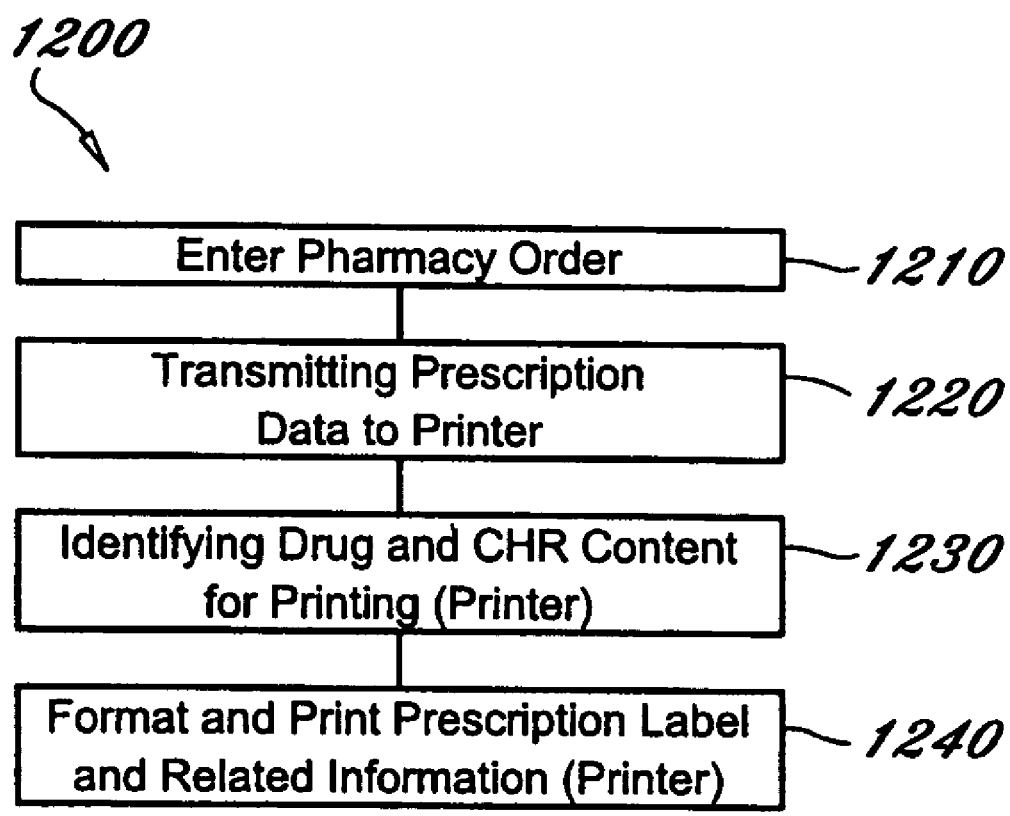
FIG. 12 is a flow chart showing at a high level novel process steps for using the network CS.

FIG. 12 shows method 1200 including in sequence, entering a pharmacy order in step 1210, transmitting prescription information to a pharmacy printer in step 1220, in the pharmacy printer, identifying drug and CHR content for printing in association with the prescription in step 1230, and then formatting and printing a prescription label and related drug and CHR content information. Either prior to step 1220, additional information relating to the prescription may be added to the prescription data, including information stored in the local CS database 30A, the central CS database 20A, or the printer database 30A, by the corresponding CPU. This information may include additional information about patient or the doctor, such as contact information or payment information.

We claim:

1. A network CS, comprising:
    a pharmacy printer located in a pharmacy store wherein said pharmacy printer stores therein a database;
    wherein said database includes a first table having first table records, each first table record having fields for CID and CHR identifier;
    wherein said database includes a second table having second records, each second record having fields for CHR content and CHR identifier;
    wherein said pharmacy printer is further configured to parse out of a prescription label print file for a prescription a prescription CID associated with said prescription;
    wherein said pharmacy printer is further configured to retrieve from said second table prescription CHR content associated with said prescription CID;
    wherein said pharmacy printer is configured to generate a prescription label print job including prescription label information specified by said prescription label print file and said prescription CHR content.

2. The network CS of claim 1 wherein at least one prescription CHR content includes an image object.

3. The network CS of claim 2 wherein said image object occupies in said printer at least one megabyte of memory.

4. The network CS of claim 2 further comprising a CHR computer remote from said local CS and said central CS, said central CS storing CHR content and CHR additional content, and structured to update said database in said pharmacy printer with updated CHR content, CHR additional content, and values in said fourth table.

5. The network CS of claim 1 wherein said database further comprises:
    a third table having third table records, each third table record having fields for CHR identifier, content, and no field for CID;
    a fourth table for storing criteria, said fourth table including records storing at least one of values and ranges of values for at least one of new/refill, refills remaining, pill count, gender, age, and date of birth; and
    said pharmacy printer is further configured to determine additional CHR content to include in said prescription label print job based upon correspondence of values in said a fourth table and said third table.

6. The network CS of claim 1 further comprising a central CS remote from said local CS, said central CS storing a master patient records.

7. A method for using a network CS, comprising:
    storing CHR content in a database in a pharmacy printer located in a pharmacy store;
    wherein said database comprises
    a first table having first table records, each first table record having fields for CID and CHR identifier and a second table having second records, each second record having fields for CHR content and CHR identifier;
    parsing, in said pharmacy printer, out of a prescription label printer file for a prescription, a prescription CID associated with said prescription;
    retrieving, in said pharmacy printer, from said database prescription CHR content associated with said prescription CID;
    generating, in said pharmacy printer, a prescription label print job including prescription label information specified by said prescription label print file and said prescription CHR content.

8. The method of claim 7 wherein said CHR content includes an image object.

9. The method claim 8 wherein said image object occupies in said printer at least one megabyte of memory.

10. The network CS of claim 8 further comprising:
    storing on a CHR computer remote from said local CS and said central CS, CHR content and CHR additional content, and
    updating, from said CHR computer, said database in said pharmacy printer with updated CHR content, CHR additional content, and criteria stored in said fourth table.

11. The method of claim 7 wherein said database further comprises:
    a third table which includes third records that do not have a field for storing CID and do have a field for storing CHR content;
    a fourth table for storing criteria, said fourth table including records storing at least one of values and ranges of values for at least one of new/refill, refills remaining, pill count, gender, age, and date of birth; and
    said pharmacy printer is further configured to determine CHR content to include in said prescription label print job based upon correspondence of values in said said fourth table and said third table.

12. The method of claim 7 further comprising storing a master patient records on a central CS remote from said local CS.

13. A network computer system, comprising:
    (1) a central CS;
    (2) a plurality of local CSs;
    wherein said central CS and said plurality of local CSs form a network in which said plurality of local CS and said central CS can communicate with one another via network protocols;
    wherein each local CS of said plurality of local CSs is associated with and proximate to a corresponding plurality of pharmacy stores, wherein each local CS of said plurality of local CSs includes a CS terminal for inputting information about pharmacy orders and a pharmacy printer for printing information relating to said pharmacy orders;

wherein each local CS of said plurality of local CSs is designed to log information about pharmacy orders including information about medicines contained in pharmacy orders;

wherein a first local CS of said plurality of local CSs includes a first pharmacy printer located in a first pharmacy store and a first pharmacy POS located in said first pharmacy store;

wherein said first pharmacy printer includes a first pharmacy printer database storing:

(1) medicine records including in each medicine record a medicine identifier in association with information about the corresponding medicine; and (2) consumer records including in each consumer record a consumer identifier in association with CHR content to be conveyed to the consumer associated with said consumer identifier;

wherein a prescription label print file for a pharmacy order for a specified prescription includes a specified medicine identifier for a specified medicine, and a specified consumer identifier for a specified consumer;

wherein said pharmacy printer is configured to generate a prescription label print job in response to receipt by said pharmacy printer of said prescription label print file, by:

(1) searching in said first pharmacy printer database for information about said specified medicine associated with said specified medicine identifier;

(2) searching in said first pharmacy printer database for information to be conveyed to said specified consumer associated with said specified consumer identifier;

(3) associating with one another prescription label information for a prescription label for said specified prescription, said information about said specified medicine, and said information to be conveyed to said specified consumer, such that said prescription label print job specifies printing by said pharmacy printer of said prescription label, said information about said specified medicine, and said information to be conveyed to said specified consumer; and wherein said first local CS generates a de-identified pharmacy order from said pharmacy order, encrypts said specified consumer identifier associated with said pharmacy order, and transmits the de-identified pharmacy order in association with the encrypted specified consumer identifier to said central CS.

14. The system of claim 13, wherein said CHR content is stored in said first pharmacy printer database in association with said specified consumer identifier.

15. The system of claim 13, wherein an identifier of said CHR content is stored in
said first pharmacy printer database association with said consumer identifier.

16. The system of claim 13 wherein said first local CS includes code instructing said first local CS to transmit to said central CS information about pharmacy orders including associated consumer identifiers and an address associated with said first local CS.

17. The system of claim 13 wherein said central CS includes code for determining from (1) criteria it stores and (2) information about pharmacy orders associated with said specified consumer identification, said CHR content to associate with said consumer identification, and said central CS includes code for transmitting an identifier of said CHR content to said first local CS.

18. The system of claim 13 wherein said central CS includes code for transmitting to said first local CS medicine records including in each medicine record a medicine identifier in association with information about the corresponding medicine.

19. The system of claim 13 wherein said first local CS includes code for storing in said first pharmacy printer database (1) medicine records including in each medicine record a medicine identifier in association with information about the corresponding medicine and (2) CHR content.

20. The system of claim 19 wherein said medicine records comprise medicine monograph data and MedGuide data.

21. The system of claim 13 wherein said CHR content includes at least one of (1) names of alternative brands of a medicine specified in prescription contained in a corresponding pharmacy order, (2) an incentive offer for a subsequent purchase of a product other than said medicine, and (3) informational messages promoting said specified medicine.

22. The system of claim 13, wherein said central CS includes code for periodically transmitting identifiers of CHR content in association with said consumer identification to said first local CS.

23. The system of claim 22, wherein said central CS includes code for automatically transmitting identifiers of CHR content that it has associated with said consumer identification to said first local CS in response to transmission from said local CS to said central CS of said consumer identification, so that said CHR content is printed by said first printer either concurrently or sequentially with printing by said first pharmacy printer of said specified prescription and information about said specified medicine.

24. The system of claim 23, wherein data storage size in said first pharmacy printer database for said specified prescription, said information about said specified medicine, and said information to be conveyed to said specified consumer exceeds ten megabytes.

25. The system of claim 23 wherein said first pharmacy printer database store local rules that the printer implements in addition to the rules instructing it to what to print based upon identifications of medicines and CIDs, wherein said local rules include at least one of (1) content local rules to print additional text or graphics upon receipt of instructions to print specified CHR content and CHR additional content and the other print file information and (2) layout local rules to lay out all of the material for printing defined by the print file information and the specified CHR content and CHR additional content, depending upon all of the material for printing, the type of printer, and print specification such as paper width and margins.

26. The system of claim 13, wherein said first local CS is inside a local area network (LAN).

27. The system of claim 26, wherein said central CS is networked to each local CSs over a wide area network.

28. The system of claim 27, wherein data transmission speed in said LAN is greater than the data transmission speed in said WAN.

29. The system of claim 13 wherein said central CS stores a master set of rules based upon printer type, material for printing, and print specifications, and includes code specifying that said central CS distributes corresponding rules to printers having corresponding printer type, material for printing, or print specifications stored by said central CS.

30. The system of claim 13 wherein said system is designed to deliver to said first pharmacy printer instructions in response to a pharmacy order for printing information for the consumer placing said first pharmacy order, transmitted by both a first local CS controller CPU in the first local CS and also from said central CS.

31. The system of claim 30 wherein said first pharmacy printer includes code to prioritize print instructions received from both said first local CS controller CPU and the central CS regarding a single pharmacy order.

* * * * *